United States Patent [19]

Schwarzberg et al.

[11] Patent Number: 5,464,749

[45] Date of Patent: Nov. 7, 1995

[54] IMMUNOASSAY OF FREE SUBSTANCES IN BIOLOGICAL FLUIDS

[75] Inventors: Moshe Schwarzberg, Hastings-on-Hudson, N.Y.; Santosh Dayal, Fair Lawn, N.J.

[73] Assignee: Bayer Corporation, Tarrytown, N.Y.

[21] Appl. No.: 733,934

[22] Filed: Jul. 22, 1991

[51] Int. Cl.$^6$ .......................... C12Q 1/00; G01N 33/53; G01N 33/536; G01N 33/538

[52] U.S. Cl. .................. 435/7.92; 435/7.93; 435/7.94; 435/962; 436/500; 436/501; 436/518; 436/817

[58] Field of Search .................................. 436/500, 518, 436/817, 501, 548; 435/7.92, 7.93, 7.94, 962

[56] References Cited

U.S. PATENT DOCUMENTS

| | | | |
|---|---|---|---|
| 4,292,296 | 9/1981 | Parsons, Jr. | 436/500 |
| 4,366,143 | 12/1982 | Midgley et al. | 436/501 |
| 4,839,299 | 6/1989 | Charlton et al. | 436/500 |

OTHER PUBLICATIONS

Free Hormones in Blood, Albertini and Ekins Ed. 1982, 73–90.
Coat–A–Count, Diagnostic Products Corporation 1983.
Cacar Lelievre et al. Diethylstilbestrol Enzyme Assay 1988, Sci. Aliments 8(1) 149–170.
Bosch et al. Enzyme Immunoassay for total oestrogens in pregnancy plasma or serum 1978. 89 pp. 59–70.
Kumar et al. An Enzyme Immunoassay for Quantitation of a Type 2 Pneumocyte–Specific Surfactant Associated Antigen . . . 1986 J. Immunassay 157–168.
Kao et al. A monoclonal Antibody Based Enzyme Linked Immunosorbent Assay for Quantitation of Plasma Thrombospondin 1186 Am. J. Clin. Pathol. Thyopoc–4, Amersham–Searle 1973.
Voller, A. et al. Manual of Clinical Immunology; See Chapter 17 pp. 99–109; 1986.

*Primary Examiner*—Christine M. Nucker
*Assistant Examiner*—Anthony C. Caputa
*Attorney, Agent, or Firm*—Sprung Horn Kramer & Woods

[57] ABSTRACT

A method of determining free analyte level in a sample containing the analyte in free and bound portions is accomplished in sequential steps as follows. The sample is combined with a known first liquid volume containing soluble anti-analyte receptor in excess of the free analyte in the sample. The resultant mixture is incubated for a period of time sufficient to allow the binding reaction of the free analyte with the anti-analyte receptor to reach substantial completion to form a first incubation mixture. A known second liquid volume is added thereafter which contains soluble conjugate sufficient to reduce the sample proportion in the resultant mixture to no greater than 10% v/v, with the conjugate comprising a labeled analyte or labeled analog thereof, to allow the conjugate to bind with the anti-analyte receptor not bound in the first incubation mixture to form a second incubation mixture. Thereafter, separation means is introduced to the second incubation mixture which comprises a solid phase coated with immobilized binder for the anti-analyte receptor, which binder is in excess of the anti-analyte receptor to bind substantially with all of the anti-analyte receptor in the incubation mixture. The solid phase is then separated and washed from the mixture. The amount of conjugate that is bound to the solid phase is measured, and the free analyte concentration in the sample is determined.

16 Claims, 1 Drawing Sheet

IMMUNOASSAY OF FREE SUBSTANCES IN BIOLOGICAL FLUIDS

BACKGROUND OF THE INVENTION

1. Field of the Invention

The present invention relates to immunoassay techniques for the direct determination of free analytes in biological fluids, and in particular, to immunoassay techniques to effect direct determination of a free analyte which overcome biases caused by excess bound analyte and unbound natural receptors present in the sample.

2. Description of the Prior Art

For the purpose of this invention, a free analyte is that portion of unbound analyte in a biological sample wherein a binding equilibrium exists between the analyte and one or more specific binding receptors naturally occurring in the sample. Ordinarily, the analyte will be firmly and reversibly bound to its receptors and the portion of bound analyte will significantly exceed the portion of free analyte in the binding equilibrium.

Numerous physiologically active and inactive substances that circulate in biological fluids such as blood or serum are firmly and reversibly bound to specific protein carriers or other receptors naturally occurring in the fluid. These substances may belong, for example, to the groups of hormones, steroids, drugs, drug metabolites, proteins, polypeptides, vitamins, toxins and alkaloids. A binding equilibrium state exists in the fluid between the substance and its receptors leading to the distribution of the substance into a bound portion and an unbound or free portion.

For most physiologically active substances, it is known that the free portion is involved in controlling the physiological response associated with those substances. During metabolic activity, which involves the consumption of a free circulating substance by tissues, the concentration of that free substance is maintained constant by the equilibrium mechanism. Therefore, determination of free analyte in biological samples is often clinically more relevant than determination of total analyte, which includes both the free and the bound portions.

A specific example may be given from the field of thyroid disease diagnosis. The thyroid hormones, thyroxine (T4) and tri-iodothyronine (T3), circulate in blood while bound to three major binding proteins: thyroxine binding globulin (TBG), thyroxine binding prealbumin (TBPA) and albumin (Alb). The bound portion of either T4 or T3 is greater than 99.5% of the total hormone, and normally, the free portion is smaller than 0.05% or 0.3%, respectively. It is evident in this case that determination of the free hormone would provide completely different information than the determination of the total hormone.

It is well known that the nature, and often the severity, of thyroid disease status is better correlated with the free thyroid hormone concentration than with the total or protein-bound thyroid hormone concentration. Furthermore, the evaluation of thyroid status in certain other conditions is more clinically efficient using the free thyroid hormone levels. Examples for such conditions are pregnancy or estrogen therapy which may lead to altered levels of total thyroid hormone and/or binding proteins.

Competitive analyte binding methods, particularly competitive binding immunoassays, are used to determine the total concentration of analytes in biological samples such as blood, plasma or serum. These methods apply immunoreactive species such as antibodies to the analyte and cross-reactive analyte conjugates to enable the measurement. In certain cases, special optimizations or the addition of releasing agents are required in order to effect the complete release of the analyte from the endogenous receptors in the sample. In comparison, immunoassay methods for determination of free analytes are designed to avoid biases frequently caused by the interaction of excess bound analyte and unbound endogenous receptors with the added immunoreactive species of the immunoassay.

Numerous patents have been issued that disclose assays for free species of substances such as thyroxine and tri-iodothyronine that are present in clinical samples in both the free and bound forms.

U.S. Pat. No. 4,366,143 to Midgley, et al. discloses a one-step immunoassay method for determination of free analyte concentration, for example, thyroxine (T4). The sample is combined simultaneously with known amounts of a labeled derivative of the ligand or analyte and a specific receptor such as an antibody. After an incubation period, the receptor is separated, and the concentration of free analyte is related to the amount of labeled analyte which becomes associated with the receptor.

The labeled derivative of the analyte is required to be bindable by the added specific receptor and to be substantially non-reactive with the naturally occurring receptors in the sample. This labeled derivative is chemically modified, for example, by providing a blocking bridge between the analyte and the label moieties so as to render it substantially non-reactive with the endogenous receptors, while retaining its ability to bind to the added specific receptor.

U.S. Pat. No. 4,292,296 to Parsons discloses a two-step immunoassay method for determination of free analyte concentration. In the first step, the sample is contacted with a specific receptor for the analyte, for example, an antibody coated on the interior of a test tube. The antibody is chosen to have high affinity constant and low binding capacity in the assay. After a first incubation period, the sample-containing liquid is removed and discarded, and the test tube is washed. In the second step, a labeled derivative of the analyte or a labeled analog of the analyte is added to the washed coated tube to bind with the remaining immobilized receptor in the test tube. After a second incubations period, the liquid phase is separated and the concentration of free analyte is related to the amount of labeled derivative associated either with the coated tube or the removed liquid.

U.S. Pat. No. 4,391,795 to Pearlman discloses a two-step immunoassay method for determination of free thyroxine in a serum sample. In the first step, the serum sample is contacted with an immobilized receptor, preferably anti-thyroxine anti-body coated on a test tube, to bind the free thyroxine hormone. After first incubation period, the sample is removed and a labeled thyroxine hormone, preferably radiolabeled, is added to bind with the remaining unbound receptor. The labeled thyroxine hormone is added in excess of the remaining binding sites of the coated binder. After a second incubation period, the liquid phase is separated, and the concentration of free thyroxine hormone in the sample is related to the amount of labeled thyroxine hormone either present in the coated tube or present in the separated liquid phase.

U.S. Pat. No. 4,410,633 to Hertle, et al. discloses a one-step immunoassay method for determination of free thyroxine or tri-iodothyronine in a liquid sample. This one-step immunoassay method is similar to the Midgley method described above in U.S. Pat. No. 4,366,143. The method uses anti-thyroxine antibody which is immobilized on a solid phase as the receptor. The labeled thyroxine derivative is a thyroxine-linked horseradish peroxidase which does not significantly interact with the thyroxine binding globulin or thyroxine binding prealbumin present in the sample. The enzymatic activity of the horseradish peroxidase label is measured.

In general, hapten-enzyme conjugates, including thyroxine-enzyme conjugates, are well known in the prior art. Specific enzyme immunoassay procedures, which utilize these conjugates, are applied for quantitation of total analyte concentration in biological samples. See, for example, U.S. Pat. Nos. 3,839,153, 3,850,752, 3,879,262 and 4,040,907.

However, in these patents, as well as in the general literature on competitive binding immunoassays, there are no suggestions or disclosures that these procedures are suitable for the determination of free hapten concentration and certainly not free thyroxine.

SUMMARY OF THE INVENTION

The present invention provides an immunoassay method for direct determination of free analyte concentration which does not require either a wash step or the use of a special blocking conjugate bridge chemistry to eliminate the interference binding of the conjugate by the naturally occurring binding proteins in the sample during the immunoassay. Surprisingly, we found that the expected interference binding may be substantially reduced or eliminated by providing for the sequential addition of assay reagents at controlled times and in controlled concentrations.

The present method can be used for determination of free analyte concentration, for example, free thyroxine, in a sample of biological fluid which contains the analyte both in free and bound portions that are in binding equilibrium with naturally occurring receptors. The method comprises the steps of:

(a) combining the sample with a known first liquid volume containing soluble anti-analyte receptor in excess of the free analyte in the sample;

(b) incubating the resultant mixture for a period of time sufficient to allow the binding reaction of the free analyte with the anti-analyte receptor to reach substantial completion to form a first incubation mixture;

(c) adding to the incubation mixture of step (b) a known second liquid volume containing soluble conjugate sufficient to reduce the sample proportion in the resultant mixture to no greater than 10% v/v, the conjugate comprising a labeled analyte or labeled analog thereof to allow the conjugate to bind with the anti-analyte receptor not bound in step (b) to form a second incubation mixture;

(d) introducing to the second incubation mixture of step (c) separation means comprising a solid phase coated with immobilized binder for the first receptor, which binder is in excess of the anti-analyte receptor to bind substantially with all of the anti-analyte receptor in the incubation mixture;

(e) separating and washing the solid phase from the mixture of step (d);

(f) measuring the amount of conjugate that is bound to the solid phase of step (e); and (g) using the measurement for determination of the free analyte concentration in the sample.

DESCRIPTION OF THE DRAWINGS

The above and other objects and significant advantages of our invention are believed made clear by the following detailed description thereof taken in conjunction with the accompanying drawings wherein.

DESCRIPTION OF THE PREFERRED EMBODIMENT

Figure 1:
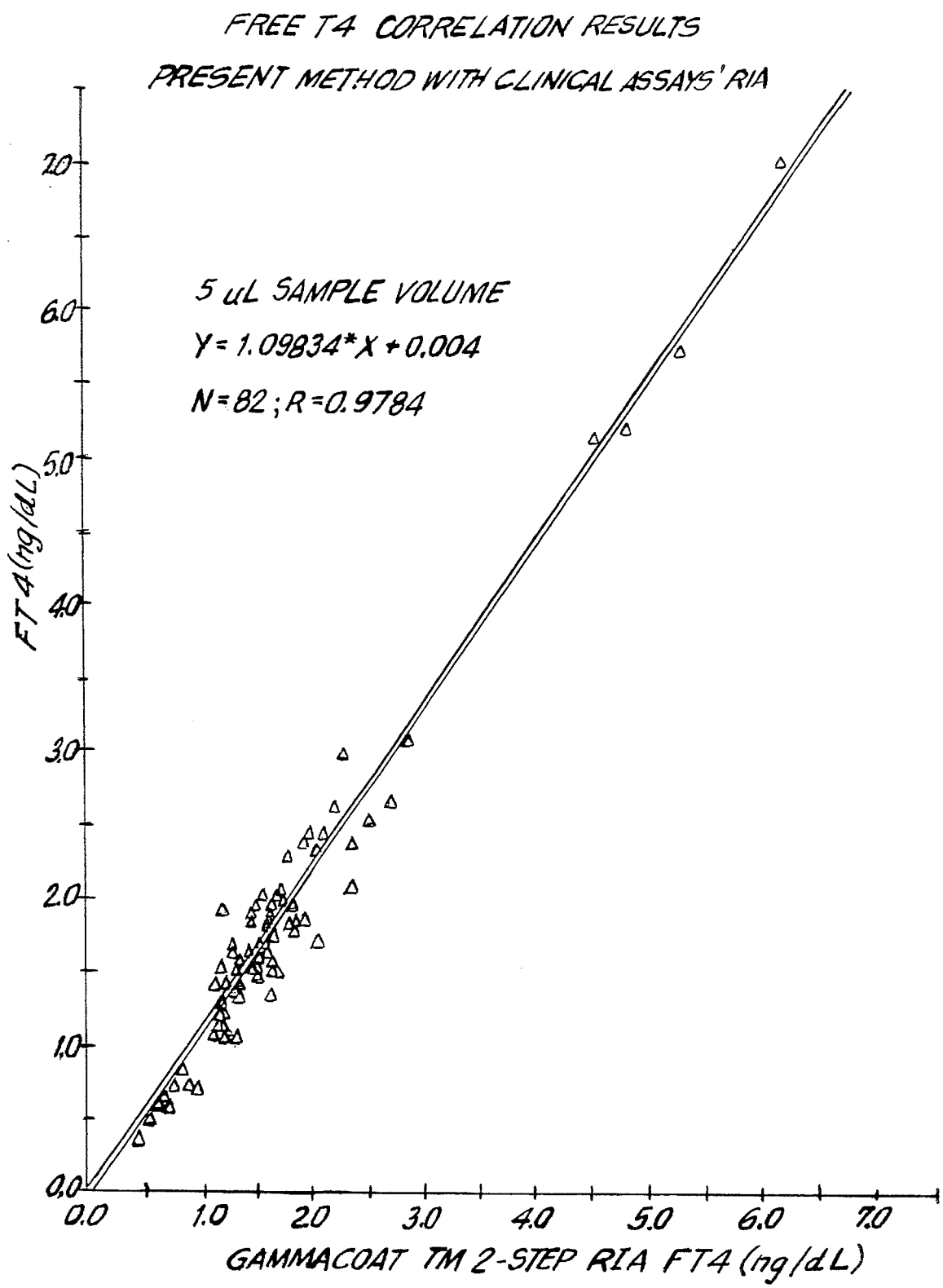
FIG. 1 is a graph illustrating the comparison reported in Example 3 between the method of the invention and the commercially available Clinical Assays kit for FT4 (Baxter-Travenol).

A significant feature of the present method is the use of a labeled analyte conjugate in immunoassays for the determination of the level of free analyte in a sample which contains both free and bound analyte without the need for removing the sample-containing mixture prior to any of the immunobinding steps.

Another significant feature is the sequential order of reagent addition. The delayed addition of conjugate permits the first binding reaction between the receptor and the ligand to proceed at reduced volume and time for better efficiency, while enabling both a further dilution of the sample and a higher concentration of conjugate than would be permissible in competitive binding immunoassays. The net effect of these advantages is to minimize or eliminate sample interference in a novel manner.

The analyte can be a hormone, a biochemical messenger, a steroid, a drug, a drug metabolite, a polypeptide, a protein, a vitamin, an alkaloid, or a mono-, di- or polysaccharide. Preferably it is a thyroid hormone, cortisol, progesterone or testosterone.

The specific receptor can be an antibody to the analyte or a reagent based upon such antibody.

The labeled derivative of the analyte can be a conjugate of an analyte or analyte analog with a non-isotopic reporting group, such as a fluor, a chromophore, an enzyme or a chemiluminescent group. Where the analyte is thyroxine or tri-iodothyronine, the labeled derivative of the analyte is preferably modified at one or both of the carboxyl group and the amino group.

The following is a description of the immunoassay for free analyte.

In the first incubation step (b) of our sequential immunoassay, an anti-analyte receptor, such as an antibody, is introduced and incubated with the sample to bind with the free analyte in the sample. The anti-analyte receptor is capable of binding with the conjugate that is introduced later to signal the immunoassay. The anti-analyte receptor is also conjugated with a non-interfering hapten, such as fluorescein, for later binding by the anti-fluorescein antibody on the solid phase. The amount of anti-analyte receptor that is incubated with the sample at this step can range from about 0.1% to 5% equivalents of the total analyte in the sample. Under this limitation, the amount of anti-analyte receptor in the incubation is in excess of the free analyte, and is insufficient to bind with the total analyte or significantly alter the existing equilibrium between the analyte and its naturally occurring receptors in the sample. The ratio of anti-analyte receptor reagent volume to sample volume and the incubation time are selected to enable the binding reaction between the free analyte and the anti-analyte receptor to proceed substantially to completion. For example, sample volume can range from about 2 to 20 microliters, and is preferably 5 microliters. The anti-analyte receptor reagent volume can range from 20 to 100 microliters, and is preferably 65 microliters. The sample to reagent ratio can range from about 1:10 to 1:20, and at the preferred volume, is 1:13 v/v. The incubation time for this step can range from about 2 to 120 minutes, and is preferably 15 minutes.

In the second incubation step (c) of the sequential immunoassay of our invention, a liquid conjugate reagent is introduced to the first incubation mixture of step (b). The conjugate comprises a reporting group, such as an enzyme, that is conjugated with an analyte derivative or a cross-reacting analog of the analyte thereof, and is capable of becoming bound by the remaining unbound anti-analyte receptor in the first incubation. The amount of conjugate is optimized to give the required assay signal and sensitivity. The volume of the conjugate-containing reagent is selected to result in further dilution of the sample in the resultant incubation mixture to no greater than 10% v/v overall. The incubation time for this step can range from 1 to 30 minutes, and is preferably 5 minutes.

In the third incubation step (d) of our sequential immunoassay, the separation solid phase is introduced to the second incubation mixture of step (c). The solid phase, such as a suspension of magnetic particles, is coated with excess anti-hapten binder, such as anti-fluorescein antibody, and is capable of binding with the hapten-conjugated anti-analyte receptor in the incubation mixture. The incubation with the solid phase is allowed to proceed for a time that is sufficient to permit the binding of substantially all of the hapten-conjugated anti-analyte receptor in the incubation mixture. This incubation time can range from about 5 to 20 minutes, and is preferably 10 minutes. The solid phase is then separated from the incubation mixture and washed. The total time from the introduction of the conjugate step (c) throughout the separation step of the solid phase step (e) can range from about 5 to 40 minutes, and is preferably 15 minutes.

The amount of reporting group or conjugate that is bound to the washed solid phase is then measured and related to the free analyte concentration in the sample of steps (f)–(g). Such monitoring and correlating steps are well known to those skilled in the art of immunoassays, and need not be described in detail herein. For example, where the label is an enzyme, the relevant substrate may be added, and the enzymatic reaction rate is measured.

Reduction of the overall immunoassay time is of interest for efficiency and increased work throughput in clinical settings. Of significant interest is the development of such immunoassays that can be adapted for use on automated clinical instruments. An automated diagnostics device which can perform homogeneous and heterogeneous analysis concurrently and on a random access basis for multiple samples using sequential reagent additions as well as solid phase separation, wash, substrate addition and measurement within the preferred incubation times as described above, has been disclosed in co-pending U.S. patent application Ser. No. 07/384,594 filed Jul. 24, 1989, and the full disclosure of automated analytical apparatus and method described therein are incorporated herein by reference. The apparatus includes a circular reaction tray supporting a multiplicity of peripherally arranged reaction cuvettes, sample handling arrangement for supporting samples to be analyzed, and a reagent tray supporting a plurality of liquid-reagent sources. The individual samples and liquid reagents are transferred, on a selective-random mode, by appropriate aspirating-dispensing apparatus, respectively, into reaction cuvettes on the reaction tray which are successively positioned at a sample and reagent addition stations. The reaction tray is rotated from the reagent addition station to allow mixing and incubation of the reaction mixture, and to position each cuvette at an analysis station. In the case of heterogeneous assays, a magnetizable particle suspension is introduced into appropriate cuvettes at a magnetizable particles addition station. A particle wash station is provided between the magnetizable particles addition station and the analysis station whereat, after the reaction, the solid phase is washed in the reaction cuvette to remove unbound materials. Following such wash, substrate is added to the reaction cuvette for reaction with the enzyme-bound magnetizable particles which are resuspended. The reaction cuvette is then advanced to the analysis station, where the magnetizable particles are withdrawn from the optical path and the appropriate optical readout of the liquid phase is effected. In respect of both heterogeneous and homogeneous assays, the rotational mode of the reaction tray is bidirectional, to provide multiple period readouts of each cuvette, to obtain data which is processed to provide the rate of the reaction.

EXAMPLES

The following examples set forth the immunoassay procedure of our invention. Standard commercially available reagent grade materials were used whenever possible. It will be understood that the reagents and the procedures which follow are provided for purpose of illustration only, and that other ingredients, proportions and procedures can be employed in accordance with the disclosures of this invention.

1. Determination of Free Thyroxine (FT4) in Human Serum.
Materials and Reagents

Reagent 1: Mouse ascites containing anti-T4 monoclonal antibody were obtained from Meloy Laboratories. The antibody was purified from the ascites by HPLC and conjugated with fluorescein isothiocyanate. The conjugated antibody was dissolved in a suitable buffer to give a concentration of 45 micrograms antibody per liter.

Reagent 2: Tri-iodothyronine (T3) was conjugated to the enzyme alkaline phosphatase using the cross-linking agent disuccinimidyl suberate (Pierce Chemical Company, U.S.A.). The conjugated enzyme was purified on G-25 Sephadex column and dissolved in a suitable buffer to give a concentration that yields optimal signal in the assay.

Magnetic Particles (MP): Polyacrylamide particles 14–24 microns were obtained from Bio-Rad Inc., California. The particles were impregnated with magnetite and coated with goat anti-fluorescein antibody. The active magnetic particles were suspended in a suitable buffer to give approximately 100 mg particles per milliliter.

Substrate: p-Nitrophenyl phosphate dissolved in trietanolamine-containing buffer at pH=9.8.

Standards: FT4 standards were prepared from T4/T3 stripped human serum that was spiked with different levels of T4. These FT4 standards were value assigned by assaying them with the Amersham FT4 RIA kit and the Clinical Assays FT4 (2-step) RIA kit.

Instrument: An automated diagnostics device capable of performing multiple sample testing, reagent additions and incubations, and magnetic particles separations, wash, substrate addition and measurement of enzymatic activity as described in the aforenoted U.S. patent application Ser. No. 07/384,594 filed Jul. 24, 1989.
Assay Methodology The FT4 immunoassay was performed on the automated instrument at 37 degrees celsius as follows:

Five (5) microliters of human serum sample are mixed with 65 microliters of Reagent 1 in a cuvette, and the mixture is incubated for 15 minutes. Then, at minute 15, 65 microliters of Reagent 2 are added, and the incubation of the resultant mixture proceeds for an additional 5 minutes. At this time the magnetic particles are introduced.

A sufficient amount of the fluorescein-conjugated anti-T4 antibody is used via Reagent 1 to bind substantially with all of the free T4 in the sample. The T3-ALP conjugate that is added sequentially via Reagent 2 is taken up by the remaining unbound anti-T4 antibody, and its amount is greater than the amount that would be established for competitive binding immunoassay with simultaneous addition of sample and reagent.

At minute 20, 20 microliters of the magnetic particles are added, and incubation of the resultant mixture proceeds for an additional 10 minutes with constant mixing. During this time, the magnetic particles that are coated with anti-fluorescein antibody bind substantially all of the fluorescein-conjugated anti-T4 antibody present in the incubation mixture.

At minute 30, the reaction is terminated by the aspiration of the supernatant from the incubation cuvette holding the magnetic particles back with the aid of a stationary magnet. The magnetic particles are then washed several times, and 300 microliters of substrate are added.

The magnetic particles are mixed and incubated with the substrate solution. The conversion rate of the substrate by the enzyme is then measured spectrophotometrically at 405 nm by taking periodic absorbance readings using magnets to clear the particles off the light path.

The enzymatic reaction rate is then used to calculate the free T4 in the sample using a standard curve composed of known standard FT4 levels.

RESULTS

The dose-response profile of the present method using different sample volumes (SV) is shown in Table 1. The data was fitted using the Rodbard curvefit method, and gave excellent curvefit correlations.

TABLE 1

| FT4 Standard (ug/dL) | SV: | Assay Response (mA/Min.) | | |
|---|---|---|---|---|
| | | 5 uL | 10 uL | 20 uL |
| 0.0 | | 181 | 178 | 165 |
| 0.26 | | 152 | 143 | 135 |
| 0.62 | | 132 | 119 | 114 |
| 1.54 | | 100 | 88 | 77 |
| 2.73 | | 80 | 67 | 57 |
| 8.84 | | 49 | 38 | 32 |
| | R = | 0.9966 | 0.9985 | 0.9982 |

2. Analysis of Patient Serum Samples: Correlation of FT4 Results With Commercially Available RIA kit (AMERLEX-M, Amersham Corporation, USA).

Twenty-three (23) human serum samples were analyzed on the automated instrument as described in Example 1. The obtained FT4 values were compared with values obtained by assaying these samples with the Amersham RIA kit according to product insert instructions. The sample volume on the automated instrument, however, could be varied. In one experiment, the selected sample volume was twenty (20) microliters, and in the second experiment, it was five (5) microliters.

RESULT

Correlation data was obtained by performing linear regression analysis. The analysis shows that correlation with the AMERLEX-M RIA kit is improved when sample volume is five (5) microliters compared with twenty (20) microliters on the automated instrument. The reduced sample volume results in greater dilution of the sample in the final incubation mixture and elimination of sample interferences. The correlation results are summarized below and are shown in FIGS. 1a and 1b.

Present method (20 ul)=0.9497 RIA−0.0567 (R=0.908; Sy.x=0.37)

Present method (5 ul)=1.2267 RIA−0.0031 (R=0.972; Sy.x=0.23)

3. Analysis of Patient Serum Samples: Correlation of FT4 Results With Commercially Available RIA kit (Clinical Assays Two-Step Method, GAMMACOAT, Baxter-Travenol Corporation, USA).

Eighty-two (82) human serum samples were analyzed on the automated instrument as described in Example 1. The obtained FT4 values were compared with values obtained by assaying these samples with the GAMMACOAT RIA kit according to product insert instructions. The sample volume selected for use on the automated instrument was five (5) microliters.

RESULTS

Correlation data was obtained by performing linear regression analysis. Excellent correlation was obtained. The results are summarized below and are shown in FIG. 1.

Present method=1.0983 RIA+0.004 (R=0.9874)

The correlation results of Example 1 and Example 2 indicate that the method of the present invention yields valid FT4 values, and is suitable for determination of FT4 in human serum samples.

Some of the advantages of the present invention evident from the foregoing description include an improved immunoassay procedure for the direct determination of free analytes in biological fluids, which techniques overcome biases caused by excess bound analyte and unbound natural receptors present in the sample.

In view of the above, it will be seen that the various objects of our invention are achieved and other advantageous results attained.

The various features and advantages of the invention are thought to be clear from the foregoing description. However, various other features and advantages not specifically enumerated will undoubtedly occur to those versed in the art, as likewise will many variations and modification of the preferred embodiments illustrated, all of which may be achieved without departing from the spirit and scope of the invention as defined by the following claims.

What is claimed is:

1. A method of determining free analyte level in a biological fluid sample which contains the analyte both in free and bound portions that are in binding equilibrium with naturally occurring analyte receptors in said fluid sample, the method comprising the sequential steps of:

(a) combining the sample with a known first liquid volume containing soluble receptor specific to the analyte in excess of the free analyte in the sample;

(b) incubating the resultant mixture for a period of time sufficient to allow the binding reaction of the free analyte with the receptor specific to the analyte to reach substantial completion to form a first incubation mixture;

(c) adding to the first incubation mixture of step (b) a known second liquid volume containing soluble conjugate sufficient to reduce the sample proportion in the resultant mixture to no greater than 10% v/v, said conjugate comprising a labeled analyte or labeled analog thereof to allow the conjugate to bind with the receptor specific to the analyte not bound in step (b) to form a second incubation mixture;

(d) introducing to the second incubation mixture of step (c) separation means comprising a solid phase coated with immobilized binder for the specific to the analyte receptor, which binder is in excess of the specific to the analyte receptor to bind substantially with all of the receptor specific to the analyte to in the incubation mixture;

(e) separating and washing the solid phase from the mixture of step (d);

(f) measuring the amount of said conjugate that is bound to the solid phase of step (e); and (g) using the measurement of step (f) for determining the free analyte concentration in the sample.

2. The method of claim 1 wherein the analyte is selected from the group consisting of a hormone, a biochemical messenger, a steroid, a drug, a drug metabolite, a polypeptide, a protein, a vitamin, an alkaloid or a mono-, di- and polysaccharide.

3. The method of claim 2 wherein the analyte is selected from the group consisting of a thyroid hormone, cortisol, progesterone and testosterone.

4. The method of claim 1 wherein the receptor specific to the analyte comprises a monoclonal antibody.

5. The method of claim 1 wherein the analyte is labeled with an enzyme, a fluor, a chromophore, or a luminophore.

6. The method of claim 1 wherein the analyte is selected from the group consisting of thyroxine and tri-iodothyrinine, and the conjugate is selected from the group consisting of derivatives of thyroxine and tri-iodothyrinine which have been modified or labled at a site selected from the group consisting of the carboxyl group, the amino group, and both the carboxyl group and the amino group.

7. The method of claim 1 wherein step (b) comprises an incubation time of about 2 to 120 minutes.

8. The method of claim 7 wherein step (b) comprises an incubation time of about 2 to 30 minutes.

9. The method of claim 8 wherein step (b) comprises an incubation time of about 15 minutes.

10. The method of claim 1 wherein step (c) comprises an incubation time of about 1 to 30 minutes.

11. The method of claim 10 wherein step (c) comprises an incubation time of about 2 to 10 minutes.

12. The method of claim 11 wherein step (c) comprises an incubation time of about 5 minutes.

13. The method of claim 1 wherein step (d) comprises an incubation time of about 1 to 60 minutes.

14. The method of claim 13 wherein step (d) comprises an incubation time of about 5 to 20 minutes.

15. The method of claim 14 wherein step (d) comprises an incubation time of about 10 minutes.

16. The method according to claim 6 wherein the analyte is thyroxine and the conjugate is selected from the group consisting of derivatives of thyroxine which have been modified or labled at a site selected from the group consisting of the carboxyl group, the amino group, and both the carboxyl group and the amino group.

* * * * *

UNITED STATES PATENT AND TRADEMARK OFFICE
CERTIFICATE OF CORRECTION

PATENT NO. : 5,464,749
DATED : November 7, 1995
INVENTOR(S) : Schwarzberg, et al.

It is certified that error appears in the above-indentified patent and that said Letters Patent is hereby corrected as shown below:

| | |
|---|---|
| Col. 9, line 13 | After " the " (first occurrence) insert -- receptor -- |
| Col. 9, line 14 | Delete " receptor ", after " the " (first occurrence) insert -- receptor -- |
| Col. 9, line 15 | Delete " receptor " |
| Col. 9, line 16 | Delete " to " (second occurrence) |
| Col. 10, line 3 | Delete " iodothyrinine " and substitute -- iodothyronine -- |
| Col. 10, line 5 | Delete " iodothyrinine " and substitute -- iodothyronine -- |

Signed and Sealed this

Sixteenth Day of April, 1996

Attest:

BRUCE LEHMAN

*Attesting Officer*    Commissioner of Patents and Trademarks